United States Patent
Diwan et al.

(10) Patent No.: US 6,200,570 B1
(45) Date of Patent: Mar. 13, 2001

(54) HERBAL FORMULATION USEFUL AS A THERAPEUTIC AND COSMETIC APPLICATIONS FOR THE TREATMENT OF GENERAL SKIN DISORDERS

(75) Inventors: Prakash Vaman Rao Diwan; Bhamidipalli Subrahmanya Sitaramam; Sistla Ramakrishna; Kondapuram Vijaya Raghavan, all of Hyderbad (IN)

(73) Assignee: Counsel of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/199,588

(22) Filed: Nov. 25, 1998

(30) Foreign Application Priority Data

Dec. 8, 1997 (IN) ......................................... 3519/97

(51) Int. Cl.⁷ ............................. A61K 35/78; A61K 7/00; A61K 7/40
(52) U.S. Cl. ...................... 424/195.1; 424/401; 514/858; 514/860; 514/861; 514/886; 514/969
(58) Field of Search ............................. 424/195.1, 401; 514/858, 860, 861, 886, 969

(56) References Cited

FOREIGN PATENT DOCUMENTS 9833494    8/1998   (WO) .

OTHER PUBLICATIONS

Sundarraj et al. Indian Phytophathol. vol. 49 (4), pp. 398–403, abstract enclosed, 1996.
Product Alert Bulletin of Jul. 22, 1996—Abra Therapeutic Lotion.

*Primary Examiner*—Christopher Tate
(74) *Attorney, Agent, or Firm*—Pearne & Gordon LLP

(57) ABSTRACT

The invention provides a herbal formulation useful as a therapeutic and cosmetic applications for the treatment of general skin disorders, the composition comprising at least two or more plant extracts in the form of oil or powder or mixtures thereof, the plant extracts being selected from the group consisting of *Gymnena sylvestrae* water extract 3 to 6 wt. %; *Tridax procumbens* water extract 3 to 6 wt. %; its methanolic extract 4 to 6 wt. %, *Allium sativum* oil hexane extract 1 to 3 wt. %; dried juice of Aloe vera 2 to 6 wt. %; *Gum Olibanum* powder in the natural form 4 to 7 wt. %; *Gum Olibanum* resinoid organic solvent extract 3 to 8 wt. %; and resinoid free *Gum Olibanum* meal 5 to 10 wt. %., optionally, including any drug having anti-inflammatory and wound healing property or mixture thereof, the drug being selected from the group consisting of Disclofenac sodium 1–3 wt. %, Salicyclic acid 1 to 4 wt. %, Piroxicam 1 to 2 wt. %, Turmeric powder 0.1 to 1 wt. %, a base containing aqueous cream or a gel containing carbopol ranging between 1 to 4 wt. %, emulsifying ointment ranging between 20 to 40 wt. %, preservatives ranging between 0.05–0.3% and a humecant ranging between 1–4 wt. %, and remaining water to make 100 wt. %.

12 Claims, No Drawings

HERBAL FORMULATION USEFUL AS A THERAPEUTIC AND COSMETIC APPLICATIONS FOR THE TREATMENT OF GENERAL SKIN DISORDERS

FIELD OF THE INVENTION

The present invention relates to a herbal cream formulation useful for therapeutic and cosmetic applications: cracked heels, dry skin disorder, skin allergies, depigmentation and anti fungal activity. In the formulation of the present invention, the herbs that are used are known to possess anti-inflammatory, antiallergic and wound healing properties. The formulation may also be useful in treating chopped hands, hyperkeratosis and minor cuts and burn wounds.

BACKGROUND OF THE INVENTION

Skin acts as a barrier between body and its environment maintaining a controlled dynamic equilibrium. Stresses imposed by environment can cause changes in skin and major purpose of creams under consideration is to help reverse these changes and maintain a normal healthy skin. Cracking of heels is a common problem, which is observed in almost all individuals in extreme winter and summer seasons in tropical climates. Skin is a protein gel hydrated in its inner most layers and largely dehydrated in its surface layer. The purpose of water in the outer corneous layer of skin is of great physiological importance in that (1) certain amount of desiccation from skin surface minimises bacterial multiplication and assists in maintaining integrity. (2) The continual desquamation of skin is nature's method of removing debris and foreign matter, which are generally embedded in skin apertures.

It is not desirable that drying of skin layer should proceed to such an extent that corneous layer prematurely flakes away and cracks develop on the skin surface.

Cracks on the heels, in extreme winter season, develop because of the closure of the pores in the outermost layers. This problem worsens if the atmosphere has low humidity. Cracks on heels are also developed in extreme summer seasons because of migration of water from innermost layers and subsequent evaporation from outer skin surface in low humid environment. In both cases, it is necessary to maintain the integrity of the skin by balancing water content in skin layers and to promote healing of fissures that develop upon prolonged exposure.

PRIOR ART DISCUSSION

In the market, at present, a number of formulations are available for cracked heels. The composition in all the preparations are different and some of them contain synthetic drugs like Salicylic acid as one of the ingredients. All the preparations are required to be used continuously for better performance of healing of the cracks developed on heels. There are some preparations, which are used for skin rashes and fungal infections between fingers and toes. Following are the preparations available with their ingredients. "Vaseline Heal Guard" of Ponds India ltd. contains the active ingredients: Salicylic Acid IP—1.5 w/w, Lactic Acid—8.0 w/w, Triclosan—0.1 w/w and Cream base-QS. "Krack" of Paras Pharmaceuticals, Kalol contains: Dodishak and Sarjaras-ab35.4%, Raktapuraka-ab3.6%, Base to make 100%. "Lichensa" by Dollar Co.P. Ltd. Chennai, contains: Clotrimazole—0.50% w/w, Menthol—1.0% w/w, Ichthammol IP66—0.20% w/w, Boric acid—1.0% w/w, Zinc oxide—5.0% w/w and Lanolin base to –100% w/w., which is also claimed as stainfree. "Link ointment" by Link, Hyderabad contains: Madhuchist—19.5%, Erandi Thail—58.5%, Karpoor—2.5% and Base—19.5%.

SUMMARY OF THE INVENTION

Accordingly, studies were undertaken to develop cream formulations containing herbal drugs and synthetic ingredients for topical application over the affected areas which will help healing of cracks on heels and also minor burn wounds and cuts on the skin. These formulations have proven usefulness in removal of pigmentation on surface of the skin and reducing the allergic reactions and can also be used in cosmetic therapy.

OBJECTS OF THE INVENTION

The objective of the present invention is to provide a herbal formulation useful for therapeutic and cosmetic applications such as cracked heels, dry skin disorder, skin allergies, depigmentation and anti fungal activity, which obviates the drawbacks of the present formulations available in the market.

Another object of the present invention is to prepare a herbal cream using the formulations of the present invention.

DETAILED DESCRIPTION OF THE INVENTION

Accordingly, the present invention provides a herbal cream formulation useful for therapeutic and cosmetic applications such as cracked heels, dry skin disorder, skin allergies, depigmentation and anti fungal activity. Which comprises plant parts or oils from medicinal plants or any drug or their mixture thereof having anti-inflammatory and would healing property like *Gymnena sylvestrae* water extract 3 to 6%, *Tridax procumbens* water extract 3 to 6% or methanolic extract 4 to 6%, *Allium sativum* (garlic) oil (Hexane extract) 1 to 3%, *Aloe vera* (dried juice) 2 to 6%, *Gum olibanum* powder in the natural state 4 to 7%, *Gum olibanum* resinoid hexane extract 4 to 6% or ethanol extract 4 to 6% or methanol extract 3 to 8% and *Gum olibanum* meal, resinoid free, (Resin extracted with methanol or ethanol or n-hexane) 5 to 10%, cream or gel bases containing carbopol-934 1 to 4%, emulsifying ointment 20 to 40%, preservatives such as methyl and propyl parabens 0.1 to 0.3% and p-chloro cresol 0.05 to 0.2%, humectants such as propylene glycol 1 to 3%, and Glycerine 1 to 4%, Diclofenac sodium 1–3%, Salicylic Acid 1 to 4%, Piroxicam 1 to 2%, Turmeric powder 0.1 to 1%.

In the embodiment of the present invention, plant extracts used may be *Gymnema sylvestrae, Ocimium sanctum, Gum olibanum, Tridax procumbens, Allium sativum, Aloe vera,* Turmeric, from any part of the plant such as leaf, root, bark, natural exudation of the bark, flower, fruit, stem or branch.

In another embodiment of the present invention the known drugs having anti-inflammatory and wound healing property used may be such as Salicylic acid, Piroxicam, Diclofenac sodium.

In still another embodiment of the present invention the base used may be such as aqueous cream base (containing emulsifying ointment BP 1993, preservative and water) or gel base (containing propylene glycol, carbopol 934 and monoethanol amine).

In yet another embodiment of the present invention the preservatives used may be such as Methyl paraben, Propyl paraben, p-Chlorocresol.

In still another embodiment of the present invention the humectants used may be as Glycerine and Propylene glycol.

As a result of intensive study conducted by the inventors with the aim of achieving afore mentioned objectives, new processes for the preparation of cream formulations for topical use were developed employing herbal drugs which are from natural origin, incorporating them into cream bases along with synthetic materials which are known to possess water retaining properties.

Accordingly, the present investigation deals with cream and gel based topical formulations. Each formulation has been described in detail giving the formula of the ingredients along with method of preparation.

The first step in the preparation of these formulations involves a process for making the plant material suitable for incorporating into cream/gel bases. The specified portion of the plant is collected and dried under shade at room temperature in an enclosed room for 72 hrs or more until the material gets dried. A specified amount of material is then extracted with solvents like n-hexane, chloroform, ethanol, methanol and water, in cold/hot condition. The choice of the solvent depends upon the type of material expected at the end of extraction process. Extraction process was carried out in a closed container immersing specified amount of the plant material in respective solvents for 72 hrs. At the end of this stage, solvent is decanted and filtered if necessary to make it free from the plant debris. The solvent is then concentrated by evaporating under vacuum at room temperature. If the solvent used is water, then concentrated solution is freeze dried to obtain the final product in powder form. If the solvent used is a non-polar solvent then final product would be an oily and viscous substance with specific physico-chemical properties. This final product is made into a formulation intended for topical use by using it as an ingredient for making creams and gels. Suitable preservatives like methyl paraben, propyl paraben and p-chlorocresol have been used. Humectants such as propylene glycol and glycerol have been used in appropriate quantities.

One embodiment of the invention provides a herbal formulation useful as a therapeutic and cosmetic applications for the treatment of general skin disorders, said composition comprising the following ingredients:

(a) at least two or more plant extracts in the form of oil or powder or mixtures thereof, the said plants extracts being selected from the group consisting of *Gymnena sylvestrae* water extract 3 to 6 wt. %; *Tridax procumbens* water extract 3 to 6 wt. %; its methanolic extract 4 to 6 wt. %, *Allium sativum* oilhexane extract 1 to 3 wt. %; dried juice of *Aloe vera* 2 to 6 wt. %; *Gum olibanum* powder in the natural form 4 to 7 wt. %; *Gum olibanum* resinoid or its organic extract 3 to 8 wt. %; and resinoid free *Gum olibanum* meal 5 to 10 wt. %.;

(b) optionally, including any drug having anti-inflammatory and wound healing property or mixture thereof, the said drug being selected from the group consisting of Disclofenac sodium 1–3 wt. %, Salicyclic acid 1 to 4 wt. %, Piroxicam 1 to 2 wt. %, Turmeric powder 0.1 to 1 wt. %;

(c) a base containing aqueous cream or a gel containing carbopol ranging between 1 to 4 wt. %, emulsifying ointment ranging between 20 to 40 wt. %, preservatives ranging between 0.05–0.3% and a humecant ranging between 1–4 wt. %; and (d) remaining water to make 100 wt. %.

The preservatives used in the above composition may be selected from the group consisting of methyl paraben, propyl paraben and p-chlorocresol. Methyl paraben and propyl paraben used as preservatives ranges between 0.1–0.3 wt. %, p-chlorocresol used may ranges between 0.05–0.2%, *Gum olibanum* resinoid hexane extract ranges between 4–6 wt. %, *Gum olibanum* resinoid methanol extract ranges between 3–8 wt. %, *Gum olibanum* resinoid ethanol extract ranges between 4–6 wt. %, glycerine used as humectant ranges between 1–4 wt. % and propylene glycol used as humectant ranges between 1–3 wt. %.

The preferred source of plant material used in the present invention is from *Gymnema sylvestrae* leaf (R. Br), *Ocimum sanctum, Gum olibanum, Tridax procumbens, Allium sativum, Aloe vera,* Turmeric.

Another embodiment of the present invention provides a herbal formulation useful for enhancing healing of burns and wounds comprising the following ingredients.

(a) plant extracts or oils from medicinal plants selected form *Tridax procumbens* water extract 3 to 6 wt. % and *Gum olibanum* powder in the natural form 4–7 wt. %;

(b) a base containing aqueous cream or a gel containing carbopol ranging between 1 to 4 wt. %, emulsifying ointment ranging between 20 to 40 wt. %, preservatives ranging between 0.05–0.3% and a humecant ranging between 1–4 wt. %;

(c) humectants selected from propylene glycol ranging between 1 to 3 wt. % and Glycerine ranging between 1 to 4 wt. %; and (d) the balance being water to mark 100 wt. %.

Yet another embodiment of the invention provides an antifungal herbal formulation comprising the following ingredients:

(a) plant extracts or oils from medicinal plants, the said plant extracts or oils being selected form *Tridax procumbens* water extract 3 to 6 wt. % or *Gum olibanum* powder in the natural form 4 to 7 wt. %;

(b) optionally any drug having anti-inflammatory and wound healing property or mixture thereof, the said drug being selected from drugs such as Disclofenac sodium 1–3 wt. %, Salicyclic acid 1 to 4 wt. %, Piroxicam 1 to 2 wt. %, Turmeric powder 0.1 to 1 wt. %;

(c) a base containing aqueous cream or a gel containing carbopol ranging between 1 to 4 wt. %, emulsifying ointment ranging between 20 to 40 wt. %, preservatives ranging between 0.05–0.3% and humecant ranging between 1–4 wt. %.

(d) humectants selected from propylene glycol ranging between 1 to 3 wt. %, and Glycerine ranging between 1 to 4 wt. %; and (e) the balance being water to make 100 wt. %.

Still another embodiment of the invention provides an anti allergic herbal formulation comprising the following ingredients:

(a) plant extracts or oils from medicinal plants, the said plant extracts or oils being selected form *Tridax procumbens* water extract 3 to 6 wt. % and *Gum olibanum* powder in the natural form 4 to 7 wt. %;

(b) a base containing aqueous cream or a gel containing carbopol ranging between 1 to 4 wt. %, emulsifying ointment ranging between 20 to 40 wt. %, preservatives ranging between 0.05–0.3% and a humecant ranging between 1–4 wt. %;

(c) humectants selected from propylene glycol ranging between 1 to 3 wt. %, and Glycerine ranging between 1 to 4 wt. %; and (d) the balance being water to make 100 wt. %.

One more embodiment of the invention provides a herbal formulation useful for cosmetic applications as moisturiser comprising the following ingredients:
- (a) plant extracts or oils from medicinal plants, the said plant extracts or oils being selected form *Gymnena sylvestrae* water extract 3 to 6 wt. % *Aloe vera* (dried juice) 206%, *Tridax procumbens* water extract 3 to 6 wt. %, *Gum olibanum* meal and *Gum olibanum* powder;
- (b) optionally any drug having anti-inflammatory and wound healing property or mixture thereof, the said drug being selected from drugs such as Turmeric powder 0.1 to 1 wt. %;
- (c) a base containing aqueous cream or a gel containing carbopol ranging between 1 to 4 wt. %, emulsifying ointment ranging between 20 to 40 wt. %, preservatives ranging between 0.05–0.3% and a humecant ranging between 1–4 wt. %;
- (d) humectants selected from propylene glycol ranging between 1 to 3 wt. %, and Glycerine ranging between 1 to 4 wt. %; and
- (e) the balance being water to make 100 wt. %.

Another preferred embodiment of the invention relates to a herbal formulation useful for therapeutic and cosmetic applications particularly discoloration comprising the following ingredients:
- (a) plant extracts or oils from medicinal plants, the plant extracts or oils being selected form *Gum olibanum* resinoid, *Tridax procumbens* water extract 3 to 6 wt. % *Gum olibanum* powder;
- (b) a base containing aqueous cream or a gel containing carbopol ranging between 1 to 4 wt. %, emulsifying ointment ranging between 20 to 40 wt. %, preservatives ranging between 0.05–0.3% and a humecant ranging between 1–4 wt. %;
- (c) humectants selected from propylene glycol ranging between 1 to 3 wt. %, and Glycerine ranging between 1 to 4 wt. %; and
- (d) the balance being water to make 100 wt. %.

The invention also, preferably, provides a process for the pre-treatment of plant material to be used as an ingredient in the herbal formulation useful as a therapeutic cosmetic application comprising:
- (a) drying the plant material under shade at room temperature for a period of about 72 hrs;
- (b) extracting the dried plant material with an appropriate solvents selected from the group consisting of h-hexane, chloroform, ethanol, methanol and water under hot or cold conditions by immersing the appropriate amount of plant material in the respective solvent for a period about 72 hrs;
- (c) decanting the solvent and filtering, if required, to make it free from plant debris;
- (d) concentrating the solvent by evaporation at room temperature or freeze drying the concentrated solution in case the solvent is water; and
- (e) obtaining the final product in oil phase or powder form from step (d) capable of being used as an ingredient for making a herbal formulation for therapeutic and cosmetic application.

The following examples are given by way of illustration and should not be construed to limit the scope of the invention.

The following are to be noted while making these formulations.

1. All the ingredients are expressed in % w/w basis.
2. Emulsifying ointment used in these formulations is prepared as per the procedure given in the official compendium (British Pharmacopoeia, 1993).

EXAMPLE-1

| | |
|---|---|
| *Tridax procumbens* leaf extract | 5% |
| Carbopol 934 | 3% |
| Methyl paraben | 0.15% |
| Propyl paraben | 0.15% |
| Monoethanolamine | q.s to bring pH to 6 |
| Propylene glycol:water(50:50) | q.s to make 100% |

The leaves of *Tridax procumbens* were shade dried for 48 hrs at room temperature. The crushed leaves (500 gms) were then soaked with water (one liter) for 72 hrs at room temperature. At the end of this period, water is decanted and then concentrated to 100 ml by evaporating under vacuum at room temperature. This concentrated solution is then lyophilised to obtain powder.

*Tridax procumbens* leaf extract is dispersed in pure propylene glycol along with propyl paraben (0.15%). The mixture is thoroughly agitated to get a clear solution. Carbopol 934 is dispersed in propylene glycol and water (50:50) mixture along with methyl paraben in another vessel. The mixture is stirred continuously at 300 rpm for 2–3 hrs. *Tridax procumbens* solution was then added and stirring was continued for about 1 hr until a gel preparation is obtained. The pH of this gel is adjusted to 6 using monoethanolamine. The gel preparation obtained is clear, transparent and non-sticky.

EXAMPLE-2

| | |
|---|---|
| *Gum olibanum* powder | 5% |
| Emulsifying ointment | 26% |
| Methyl paraben | 0.15% |
| Propyl paraben | 0.15% |
| Water | q.s to make 100% |

The naturally occurring *Gum olibanum* exudate in dry state is taken as it is. The lumps (1 Kg) were powdered in an edge runner mill for 30 minutes. The powdered raw *Gum olibanum* was passed through 100 mesh sieve. Weighed quantity of the powder was dispersed in appropriate quantity of water along with methyl paraben (0.15%). Weighed quantity of emulsifying ointment is melted in another vessel, and propyl paraben (0.15%) in dispersed in it (Oily phase). The dispersion containing *Gum olibanum* powder & methyl paraben was also heated to the same temperature as that of emulsifying ointment. The aqueous dispersion containing *Gum olibanum* powder is added to the molten emulsifying ointment and the mixture is stirred continuously at 10,000 rpm for 1 hr using homogeniser, to obtain cream consistency.

EXAMPLE-3

| | |
|---|---|
| *Gum olibanum* powder | 6% |
| *Tridax procumbens* leaf extract | 4% |

| | |
|---|---|
| Emulsifying ointment | 25% |
| Propylene glycol | 2% |
| p-Chlorocresol | 0.1% |
| Water | q.s. to make 100% |

The naturally occurring *Gum olibanum* exudate in dry state is taken as it is. The lumps (1 Kg) were powdered in an edge runner mill for 30 minutes. The powdered raw *Gum olibanum* was passed through 100 mesh sieve.

The leaves of *Tridax procumbens* were shade dried for 48 hrs at ambient temperature. The leaves (500 gms) were then soaked with water (1 liter) for 72 hrs at room temperature. At the end of this period, water is decanted and then concentrated to 100 ml by evaporating under vacuum at room temperature. This concentrated solution is then lyophilised to obtain powder.

Weighed quantity of emulsifying ointment is taken in a tarred vessel along with p-chlorocresol and heated until the ointment melts. In a separate container, *Gum olibanum* powder and *Tridax procumbens* leaf extract were dispersed in water. Required quantity of propylene glycol is also added. This aqueous mixture is heated to the same temperature as that of emulsifying ointment. The aqueous phase is then added to the oily phase, in hot condition and the mixture is stirred at 10,000 rpm for 1–3 hrs until a cream consistency is obtained.

EXAMPLE-4

| | |
|---|---|
| *Gymnema Sylvestrae* Powder | 5% |
| Salicylic Acid | 2% |
| *Gum olibanum* (n-Hexane extract) | 5% |
| Emulsifying ointment | 23% |
| Glycerol | 2% |
| p-Chlorolcresol | 0.1% |
| Water | q.s. to make 100% |

The leaves of *Gymnema Sylvestrae* were shade dried for 48 hrs at room temperature. The leaves were cut into small portions and immersed in water in a suitable vessel for 72 hrs. At the end of this period, water is decanted, filtered. This aqueous portion is then concentrated by evaporating under vacuum at 45° C. this concentrated portion is lyophilised to obtain a powder.

*Gum olibanum* lumps were powdered in 5 Kg lots in an edge runner mill for 30 minutes. The powdered raw *Gum olibanum* (250 gms) was then extracted at 30° C. using n-hexane (1.5 liters) as solvent in a vertical churner for 8 hrs. The solvent containing resinoid was then decanted and was distilled off at atmospheric pressure. The resinoid (100 gms) was obtained which is pale yellow and having a refractive index of 1.5160, density 0.9287 gms/cc and surface tension 0.0290 N/M at 30° C.

Weighed quantities of *Gum olibanum* resinoid, p-chlorocresol and emusifying ointment are taken in a container and the mixture is heated under stirring until both resinoid and emulsifying ointment melt (oil phase). *Gymnema sylvestrae* powder, salicylic acid, glycerol are dispersed in water, in a suitable container and the mixture is kept for homogenisation until a homogenous dispersion is obtained. This dispersion is heated to the same temperature as that of oil phase. This aqueous dispersion is added to the oily phase containing resinoid and emulsifying ointment in hot condition while under stirring for 1 hr at 10,000 rpm until a cream consistency is obtained.

EXAMPLE-5

| | |
|---|---|
| *Tridax procumbens* powder | 5% |
| *Gum olibanum* resinoid (Ethyl alcohol extract) | 5% |
| Tulsi Oil (*Ocimum sanctum*) | 0.5% |
| Salicylic acid | 2% |
| Methyl paraben | 0.15% |
| Propyl paraben | 0.15% |
| Propylene glycol | 2% |
| Emulsifying ointment | 25% |
| Water | q.s. to make 100% |

The leaves of *Tridax procumbens* were shade dried for 48 hrs at room temperature. The crushed leaves were then soaked with water for 72 hrs at room temperature. At the end of this period water is decanted and then concentrated to 100 ml by evaporating under vacuum. This concentrated solution is then lyophyllised to obtain a powder.

The leaves of Tulsi (*Ocimum sanctum*) were shade dried for 48 hrs and the dried leaves (1 Kg) were steam distilled to get the essential oil (yield 0.3 to 0.4%).

*Gum olibanum* lumps were powdered in 5 Kg lots in an edge runner mill for 30 minutes. The powdered raw *Gum olibanum* (250 Gms) was then extracted at 30° C. using ethyl alcohol (1.5 liters) as solvent in a vertical churner for 8 hrs. The solvent containing resinoid was then decanted and solvent was distilled off at atmospheric pressure. The resinoid (120 gms) obtained will have a density 0.940 and surface tension (N/M) 0.300.

Weighed quantities of *Gum olibanum* resinoid, Tulsi oil, propyl paraben and emulsifying ointment are taken in a container and the mixture is heated until all the ingredients melt. *Tridax procumbens* leaf extract powder, salicylic acid, methyl paraben and propylene glycol are taken along with water in a separate container and were homogenised until a homogenous dispersion is obtained. This aqueous dispersion is heated to the same temperature as that of the molten oily phase containing emulsifying ointment and other ingredients. The aqueous phase is added to the oily phase while in hot condition and dispersed using a homogeniser at 10,000 rpm for 2–3 hrs, until a cream consistency is obtained.

EXAMPLE-6

| | |
|---|---|
| Diclofenac sodium | 2% |
| *Gum olibanum* Resinoid (Methyl alcohol extract) | 4% |
| Emulsifying ointment | 29% |
| p-Chlorocresol | 0.15% |
| Water | q.s. to make 100% |

*Gum olibanum* lumps were powdered in 5 kg lots in an edge runner for 30 minutes. The powdered raw *Gum olibanum* (250 gm) was extracted at 30° C. using methyl alcohol (1.5 lt.) as solvent in a vertical churner for 8 hrs. The solvent containing resinoid was then decanted and distilled off at atmospheric pressure. The resinoid (120 gm) was obtained having density 0.940 and surface tension (N/M) 0.300.

Weighed quantities of *Gum olibanum* resinoid, emulsifying ointment and p-chlorocresol were melted until the mixture liquefies (oil phase). Diclofenac sodium was dissolved in water and heated to the same temperature as that of oil phase. The aqueous phase was then added to the oil phase while stirring in a homogenizer at 10,000 rpm, until the mass congeals and gives cream consistency.

EXAMPLE-7

| Piroxicam | 1% |
|---|---|
| Gum olibanum resinoid (Methyl alcohol extract) | 7% |
| Aloe vera | 5% |
| Emulsifying ointment | 26% |
| Glycerine | 2% |
| Propyl Paraben | 0.15% |
| Methyl Paraben | 0.15% |
| Water | q.s. to make 100% |

Gum olibanum lumps were powdered in 5 kg lots in an edge runner for 30 minutes. The powdered raw Gum olibanum (250 gm) was extracted with ethyl alcohol (1.5 lts) at 30° C. using a vertical churner for 8 hrs. The solvent containing resinoid was then decanted and distilled off at atmospheric pressure to obtain pure resinoid.

Weighed quantities of Piroxicam, Gum olibanum resinoid, dried juice of Aloe vera and emulsifying ointment are taken in a clean vessel along with propyl paraben and melted while stirring until a homogenous molten dispersion is obtained. (oil phase).

Required quantities of water, methyl paraben and glycerine were taken in a separate vessel and the mixture is heated to the same temperature as that of oily phase. The aqueous phase was then added to oily phase in hot condition and mixed in a homogenizer for 1–3 hrs at 10,000 rpm, until the resultant mass congeals to cream consistency.

EXAMPLE-8

| Tridax Procumbens (Methyl alcohol extract) | 5% |
|---|---|
| Aloe vera | 4% |
| Gum olibanum Powder | 5% |
| Emulsifying ointment | 30% |
| p-Chlorocresol | 0.15% |
| Water | q.s. to make 100% |

The leaves of Tridax Procumbens were dried under shade for 72 hrs. The dried leaves were powdered, 300 gms of powder was extracted with 1 lt of methanol in a soxhlet extractor for 6 hrs. The methanolic extract was filtered and evaporated to dryness using Rotavapor.

The naturally occurring Gum olibanum exudate in dry state is taken as it is. The lumps (1 kg) were powdered in an edge runner for 30 minutes. The powdered raw gum was passed through 100 mesh screen. The methanolic extract of Tridax procumbens, the dried juice of Aloe vera, emulsifying ointment and p-chlorocresol were taken in a vessel and heated while stirring until a molten homogenous dispersion is obtained (oily phase). Weighed quantity of Gum olibanum is dispersed in water and this dispersion is heated to the same temperature as that of oily phase. The aqueous phase is then added to the oily phase and stirred at 10,000 rpm using a homogenizer, until the resultant mass congeals to cream consistency.

EXAMPLE-9

| Gum olibanum powder | 5% |
|---|---|
| Aloe vera | 4% |
| Emulsifying ointment | 31% |
| Glycerine | 3% |
| p-Chlorocresol | 0.15% |
| Water | q.s. to make 100% |

The naturally occurring Gum olibanum exudate in dry state is taken as it is. The lumps (1 kg) were powdered in an edge runner for 30 minutes. The powdered raw Gum olibanum was passed through 100 mesh sieve. The expressed juice of Aloe vera is dried and dried juice is used in this formulation.

The dried juice of Aloe vera, emulsifying ointment and p-chlorocresol were taken in a vessel and melted while stirring occasionally (oily phase) to give a homogenous dispersion. Gum olibanum powder was dispersed in water along with glycerine. This dispersion was brought to the same temperature as that of oily phase. The aqueous dispersion was added to the oily phase while in hot condition and mixed thoroughly at 10,000 rpm using homogenizer, until the mass congeals to cream consistency.

EXAMPLE-10

| Gum olibanum resinoid (Methyl alcohol extract) | 5% |
|---|---|
| Aloe vera | 3% |
| Garlic (Allium sativum) Oil | 2% |
| Glycerine | 2% |
| p-Chlorocresol | 0.15% |
| Emulsifying ointment | 26% |
| Water | q.s to make 100% |

Gum olibanum lumps were powdered in 5 kg lots in an edge runner for 30 minutes. The powdered raw Gum olibanum (250 gm) was extracted at 30° C. using methyl alcohol (1.5 lt). The solvent containing resinoid was decanted and distilled off at atmospheric pressure to obtain the resinoid.

Weighed quantities of, Gum olibanum resinoid, dried juice of Aloe vera, garlic oil and emulsifying ointment were taken in a clean vessel along with p-chlorocresol. The ingredients were melted while mixing to get a homogeneous molten dispersion (oily phase). Specified quantity of glycerine was added to water and this aqueous phase was brought to the same temperature as that of oily phase. The aqueous phase was added to the oily phase in hot condition and mixed thoroughly at 10,000 rpm using a homogeniser, until the resultant mass congeals and solidifies to cream consistency.

EXAMPLE-11

| Gum olibanum powder | 5% |
|---|---|
| Salicylic Acid | 3% |
| Aloe vera | 3% |
| Glycerine | 2% |
| Emulsifying ointment | 27% |
| p-Chlorocresol | 0.15% |
| Water | q.s. to make 100% |

The naturally occurring Gum olibanum exudate is taken as it is. The lumps (1 kg) were powdered in an edge runner for 30 minutes. The powdered raw *Gum olibanum* was passed through 100 mesh screen.

Weighed quantities of salicylic acid dried juice of aloe vera, emulsifying ointment and p-chlorocresol were taken in a clean vessel. The ingredients were melted while stirring. *Gum olibanum* powder was dispersed in water along with glycerine. The temperature of this aqueous dispersion was brought to that of molten oily phase. The aqueous dispersion was added to the oily phase in hot condition and mixed thoroughly at 10,000 rpm using a homogenizer until the mass congeals and solidifies to cream consistency.

EXAMPLE-12

| Tridax Procumbens (water extract) | 5% |
|---|---|
| Aloe vera | 3% |
| Garlic Oil (*Allium sativum*) | 2% |
| Emulsifying ointment | 26% |
| Glycerine | 2% |
| p-Chlorocresol | 0.15% |
| Water | q.s. to make 100% |

The leaves of *Tridax procumbens* were dried under shade for 72 hrs. The leaves were crushed to powder (500 gms) and soaked with water for a week at room temperature. Water is decanted and concentrated to 100 ml by evaporation. This concentrated solution was then lyophilized to a powder.

Weighed quantities of emulsifying ointment, dried juice of *Aloe vera,* Garlic oil and p-chlorocresol were taken in a clean vessel and melted while stirring until a homogenous molten mixture is obtained (oil phase). The freeze dried leaf extract of *Tridax procumbens* was dissolved in water along with glycerine. The temperature of this aqueous solution was brought to that of oily phase. The aqueous phase was then added to oily phase in hot condition and stirred at 10,000 rpm using homogenizer, until the resultant mass congeals and solidifies to cream consistency.

EXAMPLE-13

| Gum olibanum powder | 5% |
|---|---|
| Tridax procumbens (water extract) | 4% |
| Aloe vera | 5% |
| Turmeric powder | 0.5% |
| Glycerine | 3% |
| p-Chlorocresol | 0.15% |
| Emulsifying ointment | 25% |
| Water | q.s. to make 100% |

The naturally occurring *Gum olibanum* exudate in dry state is taken as it is. The lumps (1 kg) were powdered in an edge runner for 30 minutes. The powdered raw gum was passed through 100 mesh screen.

The leaves of *Tridax procumben* were dried under shade at room temperature for 72 hrs. The leaves were crushed to powder and the powder (500 gm) was soaked with water (1 lt) for a week. Water is then decanted, filtered and concentrated to 100 ml. The concentrated solution was then lyophilized to get powder.

Weighed quantities of emulsifying ointment, dried juice of *Aloe vera,* and p-chlorocresol were taken in a clean vessel and the mixture was melted while stirring to get a molten homogenous mixture.

*Gum olibanum* powder, dry powder of *tridax procumbens* were dispersed in water along with turmeric powder and glycerine. The temperature of this aqueous dispersion was brought to that of oily phase. The aqueous phase was then added to the oily phase in hot condition, while stirring at 10,000 rpm using homogenizer, until the resultant mass congeals and solidifies to cream consistency.

EXAMPLE-14

| Tridax Procumbens (Water extract) | 5% |
|---|---|
| Aloe vera | 4% |
| Carbopol 934 | 3% |
| Methyl Paraben | 0.15% |
| Propyl Paraben | 0.15% |
| Manoethanolamine | q.s to bring pH to 6 |
| Propyleneglycol:water(50:50) | q.s to make 100% |

The leaves of *Tridax procumbens* were dried under shade for 72 hrs. The dried leaves were crushed to obtain powder. The crushed leaf powder (250 g) was soaked in water (1 lt) for a week.

Water is then decanted and concentrated to 100 ml by evaporating under vacuum at room temperature. The concentrated solution is then lyophilized to obtain powder.

The dried leaf extract of *Tridax Procumbens,* the dried juice of *Aloe vera,* propyl paraben were dissolved in pure propylene glycol by vigorous mixing using a stirrer. Carbopol 934 was dispersed separately in propylene glycol and water mixture (50:50) along with methyl paraben in another vessel. The mixture is stirred continuously for 1–3 hrs at 300 rpm using mechanical stirrer or homogenizer. The pure propylene glycol solution containing *tridax procumbens, Aloe vera* and propyl paraben was then added and stirring was continued for 1 hr until a gel preparation was obtained. The pH of this gel is adjusted to 6.0 using monoethanol amine. The final gel preparation will be clear, transparent and non-sticky.

EXAMPLE-15

| Gum olibanum Meal (Resinoid free Gum olibanum) | 9% |
|---|---|
| Aloe vera | 5% |
| Salicylic Acid | 2% |
| Emulsifying ointment | 25% |
| Methyl paraben | 0.15% |
| Propyl paraben | 0.15% |
| Water | q.s. to make 100% |

Weighed quantities of *Gum olibanum* Meal (resinoid free), *Aloe Vera,* Emulsifying ointment and Propyl paraben were taken in a tarred vessel and melted while stirring (Oily phase). Specified quantities of salicylic acid and methyl paraben were dispersed in water with the aid of heating until the temperature reaches to that of oily phase. This dispersion is added to molten oily phase while stirring at 10,000 rpm using homogenizer until the mass congeals and solidifies to cream consistency.

EXAMPLE-16

| | |
|---|---|
| *Gum Olibanum* Meal (Resinoid free) | 9% |
| *Tridax procumbens* | 5% |
| Turmeric Powder | 0.5% |
| p-Chlorocresol | 0.15% |
| Propylene glycol | 2% |
| Emulsifying ointment | 27% |
| Water | q.s. to make 100% |

Weighed quantities of *Gum olibanum* Meal (resinoid free), Emulsifying ointment and p-Chlorocresol were taken in a clean tarred vessel and melted (Oily phase).

The leaves of *Tridax procumbens* were shade dried for 48 hrs. at room temperature. The crushed leaves (500 gms) were then soaked with water (1 litter) for 72 hrs. at room temperature. At the end of this period, water is decanted and then concentrated to 100 ml by evaporating under vacuum at room temperature. This concentrated solution is then lyophilised to obtain powder.

*Tridax procumbens* extract and Turmeric powder were dispersed in water along with Propylene glycol. The temperature of this aqueous dispersion was brought to that of oily phase. This aqueous dispersion was added to molten oily phase and stirred continuously at 10,000 rpm until the mass congeals and solidifies to cream consistency.

The formulations have a varied degree of therapeutic activity on cracked heels, dry skin disorders, skin allergies, depigmentation on the surface of skin and anti-fungal action.

The formulations of the present invention are not a mere admixture resulting in mere aggregation of the properties of individual ingredients but in a synergistic mixture resulting in enhanced curative properties.

The herbal cream of the present invention was applied twice daily (morning and evening) to the crack heel of a patient for about 17 days and it was observed that the cracks on the heel were cured.

Likewise, another patient having badly cracked sole was treated with the herbal composition of the present invention for about 21 days. The herbal cream was applied twice daily i.e. once in the morning and once in the evening after cleaning the sole with soap and water. The cracked sole was healed after the period.

Another patient was treated for cracked heel for 4 days with the herbal composition of the present invention. The patient's heel was cleaned with soap and water before applying the herbal cream twice daily. The cracks appeared on the sole were healed after the treatment.

A female patient having badly cracked sole was treated with the herbal composition of the present invention for 15 days. At the end of the treatment period, it was observed that cracks on the sole disappeared.

Yet another patient having a deep crack on a toe was treated with the herbal composition for 17 days and at the end of the treatment, it was observed that the crack on a toe healed completed.

Another patient having fungal infection on sole was treated with the herbal composition of the present invention for 50 days and during the course of the treatment, it was observed that the infection was gradually reduceing. At the end of the period of the treatment, the fungal infection on the sole has completely disappeared.

The following table 2 provides a few more illustrations of treating cracked heels:

TABLE 1

Case studies for the herbal ointment formulation(16)

| Parameters | Formulations selected from the example | Totals number of patients | Number of cured patients | Results | Remarks |
|---|---|---|---|---|---|
| Cracked heels | Formulations 2–16 for cracked heels | 125 | 124 | 15–30 days | Rough skin becomes smooth and healthy. Recurrence observed in only one case. |
| Pain associated with cracked hells | Formulations 2–16 for cracked heels | 6 | 6 | 4–8 days | Relives pain quickly |
| Irritation and bleeding associated with cracked heels | Formulations 2–16 for cracked heels | 10 | 10 | 2–4 days | Quick relief from bleeding and lessens irritation |
| Depigmentation | Formulations 3, 8, 9, 13 and 14 | 4 | 4 | 30–60 days | Cure depends on the extent of pigmentation |
| Anti fungal property and fissures between toes | Formulations 1, 3, 8, 9, 12 and 13 | 8 | 8 | 20–40 days | Healing depends on severity |
| Moisturising effect | Formulations 4, 5, 8, 9, 11, 14, 15 and 16. | 30 | 30 | Immediate effect | Effect is observed immediately after the application on skin surface |
| Insect bite and allergy | Formulations 1, 5, 9 and 13 | 10 | 10 | Quick response | Reduces irritation caused to the skin |
| Superficial burns | Formulations 1, 3, 9, 12 and 14 | 5 | 5 | Quick | Patent feels cool after the application and smoothern the surface of skin |
| Wound healing property in animals | Formulations 1, 3, 9, 12 and 14 | 6 | 6 | Complete healing of excision wounds 12–14 days | Excision wounds heal by contraction and epithelization |

TABLE 2

| Number of Patents. | | Complete cure |
|---|---|---|
| (2) | 26.3.97 | 11.4.97 |
| (3) | 26.3.97 | 18.4.97 |
| (17) | 07.4.97 | 10.4.97 |
| (25) | 27.3.97 | 10.04.97 |

Table 3 given herebelow provides further examples of treatment fungal infection on human beings:

TABLE 3

| Number of Patents | Start | Complete cure |
|---|---|---|
| (60) | 21.7.97 | 10.9.97 |

The following details provide data of clinical trials conducted in respect of the present invention. The herbal ointment of the present invention has been tried for healing of cracked heels, depigmentation of skin, skin rashes and fungal infections.

Human studies:

(1) Cracked heels:

The effect of the ointment is observed in terms closure of cracks relieving pain, bleeding in severe cracks and smoothening of hardened surface. The effect was observe within 2 days of application. The pain completely subsided within 3–4 days and surface becomes very smooth.

The reappearance of cracks was not observed after the discontinuation of medicine during the observation period of 12 months except in 3 cases our of 136 cases.

(2) Depigmentation:

The black spot on the face, knee, forearm was completely cured in a period of 2 to 3 months in six individuals.

(3) Skin rashes, minor cuts and burns:

The irritation caused by insect bite (Mosquito) was nullified by the ointment in couple of minutes in about 20 patients. It was also observed that the ointment is effective against minor cuts and burns.

(4) Fungal infection:

In 6 cases the fungal infection involving irritation, painful open wounds on the foot and fissures in between fingers were subsided within 4 to 5 days and took about 2–3 months for the complete relief from open wounds and fissures.

Animal stuides:

The topical application on excision wounds on dorsal surface of wistar rats reduced the time taken for healing when compared to control wounds with respect to the parameters such as wound contraction, epithelisation and scar formation. The above study indicates that the ointment has pro healing property.

ADVANGAGES

1. The present formulations, apart from healing the cracks on heels, are useful in arresting the bleeding due to cracks and reducing the pain.
2. Once the cracks on heels are cured, the recurrence of cracks is minimum, compared to commercially available products in the market.
3. The present formulations have moisturising effect on skin and hence can be used for dry skin disorders in cosmetic therapy.
4. The present formulations have antifungal activity and hence can be used for fungal infections on skin.
5. The present formulations provide excellent protection from darkening of skin due to minor cuts, burns, wounds and pimples.
6. The present formulations have good antiallergic activity in case of insect bites, rashes and reduce itching on the skin.
7. The present formulations can be used as base material in which ingredients have analgesic and antiinflammatory property can be incorporated for potentiation of their activities.

What is claimed is:

1. An herbal formulation useful for therapeutic and cosmetic applications for the treatment of general skin disorders comprising the following ingredients:

(a) at least two or more plant extracts in the form of an oil or powder or mixtures thereof, the plant extracts being selected from the group consisting of *Gymnena sylvestre* water extract 3 to 6 wt. %; *Tridax procumbens* water extract 3 to 6 wt. %; *Tridax procumbens* methanolic extract 4 to 6 wt. %; *Allium sativum* oil-hexane extract 1 to 3 wt. %; dried juice of *Aloe vera* 2 to 6 wt. %; *Gum olibanum* powder in the natural form from 4 to 7 wt. %; *Gum olibanum* resinoid organic solvent extract 3 to 8 wt. %; and resinoid-free *Gum olibanum* meal 5 to 10 wt. % wherein at least one of the two or more plant extracts is either an extract from *Tridax procumbens* or from *Gum olibanum;*

(b) optionally, including a drug having anti-inflammatory and wound healing properties, the drug being selected from the group consisting of Disclofenac sodium 1 to 3 wt. %, Salicylic acid 1 to 4 wt. %, Piroxicam 1 to 2 wt. % and Turmeric powder 0.1 to 1 wt. %, or a mixture thereof;

(c) a base containing an aqueous cream or a gel containing carbopol ranging between 1 to 4 wt. %, emulsifying ointment ranging between 20 to 40 wt. %, one or more preservatives ranging between 0.05 to 0.3 wt. % and a humectant ranging between 1 to 4 wt. %; and (d) the balance being water to make 100 wt. %.

2. An herbal formulation as claimed in claim 1 wherein the one or more preservatives are selected from the group consisting of methyl paraben, propyl paraben and p-chlorocresol.

3. An herbal formulation as claimed in claim 2 wherein the preservative is p-chlorocresol and ranges between 0.05 to 0.2 wt. %.

4. An herbal formulation as claimed in claim 1 wherein the preservatives are methyl paraben and propyl paraben and range between 0.1 to 0.3 wt. %.

5. An herbal formulation as claimed in claim 1 wherein the *Gum olibanum* resinoid organic solvent extract is *Gum olibanum* resinoid hexane extract and ranges between 4 to 6 wt. %.

6. An herbal formulation as claimed in claim 1 wherein the *Gum olibanum* resinoid organic solvent extract is *Gum olibanum* resinoid methanol extract and ranges between 3 to 8 wt. %.

7. An herbal formulation as claimed in claim 1 wherein the *Gum olibanum* resinoid organic solvent extract is *Gum olibanum* resinoid ethanol extract and ranges between 4 to 6 wt. %.

8. An herbal formulation as claimed in claim 1 wherein the general skin disorders are selected from the group consisting of cracked heels, discoloration, dry skin disorders, fungal infections and skin allergies.

9. An herbal formulation as claimed in claim 1 wherein the humectant is glycerine and ranges between 1 to 4 wt. %.

10. An herbal formulation as claimed in claim 1 wherein the humectant is propylene glycol and ranges between 1 to 3 wt. %.

11. An herbal formulation as claimed in claim 1 which is in the form of an emulsion of cream for application to the skin.

12. An herbal formulation as claimed in claim 1 useful in enhancing the healing of cracked heels with minimum recurrences.

* * * * *

UNITED STATES PATENT AND TRADEMARK OFFICE
CERTIFICATE OF CORRECTION

PATENT NO.     : 6,200,570 B1                                             Page 1 of 1
DATED          : March 13, 2001
INVENTOR(S)    : Diwan et al.

It is certified that error appears in the above-identified patent and that said Letters Patent is hereby corrected as shown below:

<u>Title page,</u>
Item [73], delete "Counsel of Scientific and Industrial Research" and insert
-- Council of Scientific and Industrial Research --.

Signed and Sealed this

Eighth Day of April, 2003

JAMES E. ROGAN
*Director of the United States Patent and Trademark Office*